United States Patent
Mitchell et al.

(10) Patent No.: US 9,638,631 B2
(45) Date of Patent: May 2, 2017

(54) SPECIES SPATIAL RECONSTRUCTION FOR EXHAUST SYSTEM USING SPECTROSCOPY AND TOMOGRAPHY

(71) Applicant: Cummins Emission Solutions, Inc., Columbus, IN (US)

(72) Inventors: Douglas A. Mitchell, Indianapolis, IN (US); Mihai Chiruta, Madison, WI (US)

(73) Assignee: CUMMINS EMISSION SOLUTIONS, INC., Columbus, IN (US)

(*) Notice: Subject to any disclaimer, the term of this patent is extended or adjusted under 35 U.S.C. 154(b) by 0 days.

(21) Appl. No.: 14/300,429

(22) Filed: Jun. 10, 2014

(65) Prior Publication Data
US 2015/0355080 A1 Dec. 10, 2015

(51) Int. Cl.
| | | |
|---|---|---|
| *G01N 21/00* | (2006.01) | |
| *G01N 21/3504* | (2014.01) | |
| *F01N 11/00* | (2006.01) | |
| *F01N 13/00* | (2010.01) | |
| *G01N 21/35* | (2014.01) | |

(52) U.S. Cl.
CPC ......... *G01N 21/3504* (2013.01); *F01N 11/00* (2013.01); *F01N 13/008* (2013.01); *F01N 2550/02* (2013.01); *F01N 2560/12* (2013.01); *F01N 2570/18* (2013.01); *F01N 2900/1616* (2013.01); *G01N 2021/3595* (2013.01); *Y02T 10/47* (2013.01)

(58) Field of Classification Search
CPC ......... G01N 21/3504; G01J 3/42; F01N 11/00
USPC .................................................. 356/436–438
See application file for complete search history.

(56) References Cited

U.S. PATENT DOCUMENTS

| | | | | |
|---|---|---|---|---|
| 4,205,550 A | * | 6/1980 | Swanson | G01N 21/534 356/438 |
| 6,244,743 B1 | | 6/2001 | Baath | |
| 8,255,169 B2 | | 8/2012 | Hofvander et al. | |
| 2004/0261374 A1 | * | 12/2004 | Bailey | B01D 46/0058 55/302 |
| 2007/0229834 A1 | * | 10/2007 | Patel et al. | 356/432 |
| 2007/0273882 A1 | * | 11/2007 | Smith | 356/437 |
| 2010/0238445 A1 | * | 9/2010 | Roux et al. | 356/436 |
| 2010/0241361 A1 | * | 9/2010 | Hofvander et al. | 702/24 |
| 2011/0206258 A1 | * | 8/2011 | Chen et al. | 382/131 |
| 2013/0213013 A1 | * | 8/2013 | Mitchell et al. | 60/276 |
| 2014/0053538 A1 | * | 2/2014 | Reeves et al. | 60/286 |

FOREIGN PATENT DOCUMENTS

DE 199 44 006 A1 3/2001

* cited by examiner

*Primary Examiner* — Hina F Ayub
(74) *Attorney, Agent, or Firm* — Foley & Lardner LLP

(57) ABSTRACT

A system for species concentration spatial reconstruction for an exhaust system includes an emitter, a detector, and a controller. The emitter is coupled to a first portion of the exhaust system and tuned to a specific wavelength of a species to be measured. The detector is coupled to a second portion of the exhaust system opposite to the first portion such that the detector is positioned to detect a beam attenuation of a beam from the emitter. The controller is configured to receive a plurality of beam attenuation measurements from the detector and to generate a cross-sectional species concentration map based on the plurality of beam attenuation measurements.

20 Claims, 8 Drawing Sheets

SPECIES SPATIAL RECONSTRUCTION FOR EXHAUST SYSTEM USING SPECTROSCOPY AND TOMOGRAPHY

TECHNICAL FIELD

The present application relates generally to the field of selective catalytic reduction (SCR) systems for an exhaust system. More specifically, the present application relates to non-intrusive species spatial reconstruction for an exhaust system.

BACKGROUND

For internal combustion engines, such as diesel engines, nitrogen oxide ($NO_x$) compounds may be emitted in the exhaust. To reduce $NO_x$ emissions, a SCR process may be implemented to convert the $NO_x$ compounds into more neutral compounds, such as diatomic nitrogen, water, or carbon dioxide, with the aid of a catalyst and a reductant. The catalyst may be included in a catalyst chamber of an exhaust system, such as that of a vehicle or power generation unit. A reductant, such as anhydrous ammonia, aqueous ammonia, or urea is typically introduced into the exhaust gas flow prior to the catalyst chamber. To introduce the reductant into the exhaust gas flow for the SCR process, an SCR system may dose or otherwise introduce the reductant through a dosing module that vaporizes or sprays the reductant into an exhaust pipe of the exhaust system up-stream of the catalyst chamber.

In operation, the injected reductant and exhaust gas typically mix in a decomposition reaction chamber or tube such that the injected reductant can be processed into ammonia and mix with the $NO_x$ of the exhaust gas. To maximize reduction of $NO_x$ emissions by the SCR catalyst, a substantially constant ammonia to NOx ratio (ANR) distribution throughout a cross-section prior to the SCR catalyst may be preferred. Depending on how the reductant is dosed, the configuration of a dosing module and/or decomposition reaction chamber or tube, and/or other factors, the resulting exhaust gas-reductant composition can vary along the exhaust system and at cross-sections of the exhaust system. This may result in a variable ANR distribution along the exhaust system and at cross-sections of the exhaust system.

SUMMARY

One implementation relates to a system for species concentration spatial reconstruction for an exhaust system. The system includes an emitter coupled to a first portion of the exhaust system. The emitter is tuned to a specific wavelength of a species to be measured. The system further includes a detector coupled to a second portion of the exhaust system. The detector is opposite to the first portion and positioned to detect a beam attenuation of a beam from the emitter. The system still further includes a controller configured to receive a plurality of beam attenuation measurements from the detector and to generate a cross-sectional species concentration map based on the plurality of beam attenuation measurements.

Another implementation relates to an apparatus for $NH_3$ concentration spatial reconstruction for an exhaust system. The apparatus includes an emitter coupled to a first portion of the exhaust system. The emitter is tuned to a specific wavelength of $NH_3$. The apparatus also includes a detector coupled to a second portion of the exhaust system. The detector is opposite to the first portion and positioned to detect a beam attenuation of a beam from the emitter. The apparatus further includes a controller configured to receive a plurality of beam attenuation measurements from the detector and to generate a cross-sectional $NH_3$ concentration map based on the plurality of beam attenuation measurements.

Yet a further implementation relates to a method for species concentration spatial reconstruction for an exhaust system. The method includes receiving a plurality of beam attenuation measurements from a detector coupled to an exhaust system. The detector detects a beam attenuation of an emitter tuned to a specific wavelength of a species to be measured. The method further includes generating a sinogram based on the plurality of beam attenuation measurements. A cross-sectional species concentration map is generated based on an inverse Radon Transform of the generated sinogram.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

Figure 1:
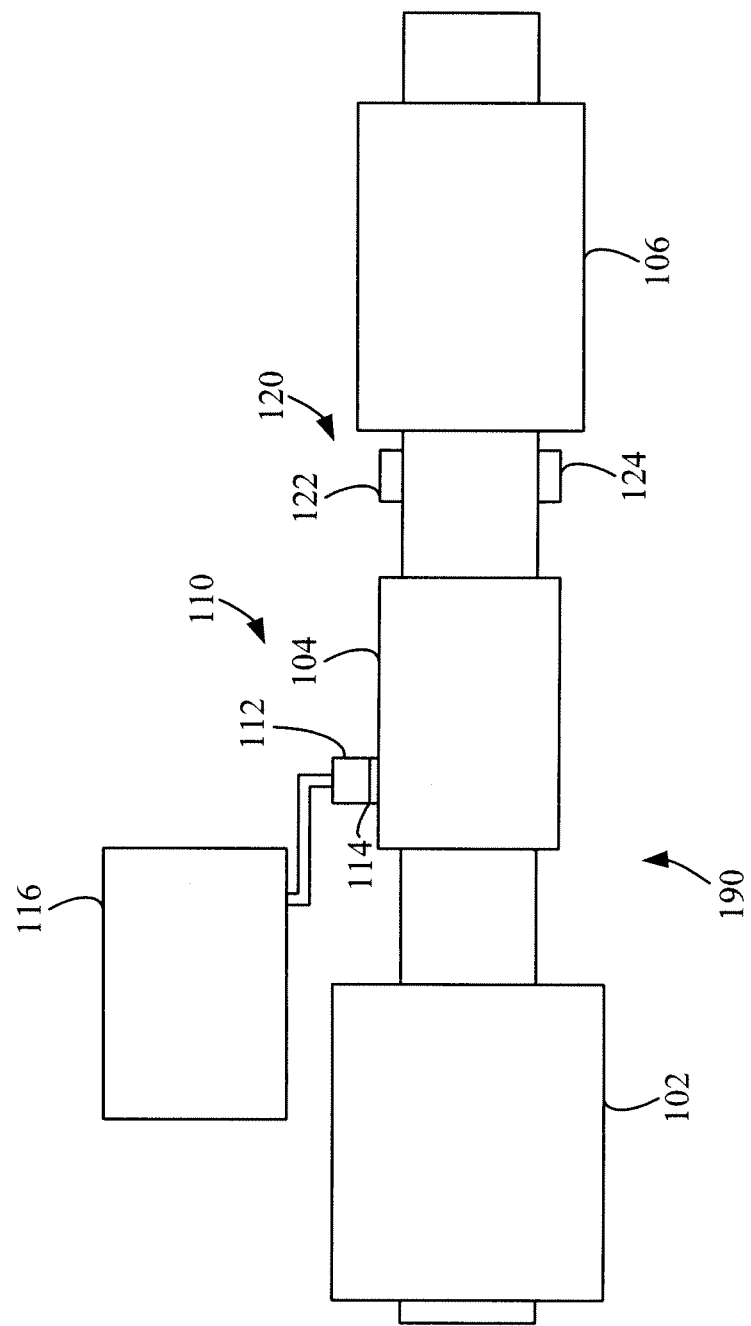
FIG. 1 is a block schematic diagram of a selective catalytic reduction system having a reductant delivery system for an exhaust system and an absorption spectroscopy measurement system.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

Following below are more detailed descriptions of various concepts related to, and implementations of, methods, apparatuses, and systems for non-intrusive species spatial reconstruction using absorption spectroscopy and tomography. The various concepts introduced above and discussed in greater detail below may be implemented in any of numerous ways, as the described concepts are not limited to any particular manner of implementation. Examples of specific implementations and applications are provided primarily for illustrative purposes.

I. Overview

To maximize reduction of $NO_x$ emissions by the SCR catalyst, a substantially constant ANR distribution throughout a cross-section prior to the SCR catalyst may be preferred. Depending on how the reductant is dosed, the configuration of a dosing module and/or decomposition reaction chamber or tube, and/or other factors, the resulting exhaust gas-reductant composition can vary along the exhaust system and at cross-sections of the exhaust system. This may result in a variable ANR distribution along the exhaust system and at cross-sections of the exhaust system. Thus, various systems and methods are provided herein for determining the ANR distribution to evaluate exhaust system and/or component designs, detect obstructions or other problems within existing exhaust systems, indirectly determine the wear on components of existing exhaust system, and/or otherwise assist in improving or diagnosing problems with an exhaust system.

Measuring ammonia, $NH_3$, can be an indirect measure of an ANR distribution assuming $NO_x$ distribution within an exhaust system is substantially uniform. Accordingly, it may be useful to provide an ammonia measurement system that can measure the ammonia distribution at a cross-sectional area of the exhaust. Such distributions may be measured at any point of the exhaust system, such as upstream or downstream of a catalyst (e.g., a SCR catalyst, a hydrolysis catalyst, etc.). In some implementations, such measurements utilize probes inserted into the exhaust system. Such probes can be maneuvered to various points within the exhaust system to measure the concentration of ammonia and the discrete measured points can be used with algorithms to substantially reconstruct the ammonia distribution (and therefore the ANR distribution) within the exhaust system. However, such probes may disrupt the exhaust gas-reductant composition flow within the exhaust system, thereby potentially altering the resulting ANR distribution.

In some implementations, absorption spectroscopy may be utilized to detect the amount of ammonia present within an exhaust system. For instance, a laser emitter and a detector may be positioned at opposing sides of a portion of the exhaust system, either at a portion of an existing exhaust system or on a testing unit that may be inserted into an exhaust system. The laser emitter may be tuned to a specific wavelength of the species of interest, such as ammonia.

II. Overview of Aftertreatment System

FIG. 1 depicts an aftertreatment system 100 having an example reductant delivery system 110 for an exhaust system 190. The aftertreatment system 100 includes a diesel particulate filter (DPF) 102, the reductant delivery system 110, a decomposition reaction chamber or reactor 104, and a SCR catalyst 106.

The DPF 102 is configured to remove particulate matter, such as soot, from exhaust gas flowing in the exhaust system 190. The DPF 102 includes an inlet, where the exhaust gas is received, and an outlet, where the exhaust gas exits after having particulate matter substantially filtered from the exhaust gas and/or converting the particulate matter into carbon dioxide.

The decomposition reaction chamber 104 is configured to convert a reductant, such as urea, aqueous ammonia, or diesel exhaust fluid (DEF), into ammonia. The decomposition reaction chamber 104 includes a reductant delivery system 110 having a dosing module 112 configured to dose the reductant into the decomposition reaction chamber 104. In some implementations, the urea, aqueous ammonia, DEF is injected upstream of the SCR catalyst 106. The reductant droplets then undergo the processes of evaporation, thermolysis, and hydrolysis to form gaseous ammonia within the exhaust system 190. The decomposition chamber 104 includes an inlet in fluid communication with the DPF 102 to receive the exhaust gas containing $NO_x$ emissions and an outlet for the exhaust gas, $NO_x$ emissions, ammonia, and/or remaining reductant to flow to the SCR catalyst 106.

The decomposition chamber 104 includes the dosing module 112 mounted to the decomposition reaction chamber 104 such that the dosing module 112 may dose a reductant, such as urea, aqueous ammonia, or DEF, into the exhaust gases flowing in the exhaust system 190. The dosing module 112 may each include an insulator 114 interposed between a portion of the dosing module 112 and the portion of the decomposition reaction chamber 104 to which the dosing module 112 is mounted. The dosing module 112 is fluidly coupled to one or more reductant sources 116. In some implementations, a pump (not shown) may be used to pressurize the reductant source 116 for delivery to the dosing module 112.

The dosing module 112 is also electrically or communicatively coupled to a controller (not shown). The controller is configured to control the dosing module 112 to dose reductant into the decomposition reaction chamber 104. The controller may include a microprocessor, an application-specific integrated circuit (ASIC), a field-programmable gate array (FPGA), etc., or combinations thereof. The controller may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller can read instructions. The instructions may include code from any suitable programming language.

The SCR catalyst 106 is configured to assist in the reduction of $NO_x$ emissions by accelerating a $NO_x$ reduction process between the ammonia and the $NO_x$ of the exhaust gas into diatomic nitrogen, water, and/or carbon dioxide. The SCR catalyst 106 includes inlet in fluid communication with the decomposition reaction chamber 104 from which exhaust gas and reductant is received and an outlet in fluid communication with an end 192 of the exhaust system 190.

The exhaust system 190 may further include a diesel oxidation catalyst (DOC) in fluid communication with the exhaust system 190 (e.g., downstream of the SCR catalyst 106 or upstream of the DPF 102) to oxidize hydrocarbons and carbon monoxide in the exhaust gas.

The exhaust system 190 further includes an absorption spectroscopy measurement system 120. The absorption spectroscopy measurement system 120 may be located at any point on the exhaust system 190, such as upstream and/or downstream of a catalyst, or the absorption spectroscopy measurement system 120 may be utilized with any other system having a fluid flowing therein. The absorption spectroscopy measurement system 120 includes an emitter 122 and a detector 124. Species uniformity measurement, such as uniformity of ammonia within the exhaust system 190, has become an important consideration to evaluate an emissions device on how a species distribution on a catalyst affects system performance. Species uniformity utilizes knowledge of the two dimensional concentration profiles for each species. The absorption spectroscopy measurement system 120 is a non-interfering, non-intrusive system 120 that can increase both the accuracy and the speed of species uniformity measurement. Each species has a specific absorption profile that allows it to be identified and determine its concentration. Fourier Transform-Infrared (FTIR) system uses this principle. The emitter 122 may include an infrared (IR)-laser that is configured and tuned to measure $NH_3$, for example, HNCO, or any other species to be detected by the absorption spectroscopy measurement system 120. The emitter 122 creates a beam at the specific wavelength as $NH_3$, HNCO, or any other species to be detected. This beam shines through the exhaust gas within the exhaust system 190 and the detector 124 measures the relative strength of the beam from the emitter 122. The intensity of the beam lost can then be correlated to the species' concentration within the exhaust gas from the emitter 122 to the detector 124. This beam attenuation can be measured at several different angles and/or linear locations to develop the two dimensional concentration profiles, as will be discussed in greater detail herein.

The absorption spectroscopy measurement system 120 can include a small interrogation window formed through the exhaust system 190 at the emitter 122 and the detector 124 to permit the laser beam through. In some implementations, the absorption spectroscopy measurement system 120 may be mounted directly to the exhaust system 190 by forming the interrogation windows in opposing sides of an exhaust tube of the exhaust system 190. The emitter 122 and detector 124 may then be mounted (e.g., via mounting hardware, such as bolts, screws, clamps, etc.) and adjusted to allow the beam from the emitter 122 to be detected by the detector 124. In some instances, an insulator may be provided to insulate the emitter 122 and/or detector 124 from heat from the exhaust system 190. In other implementations, a sealant may be included to seal the exhaust system 190 to substantially prevent exhaust gases from escaping. In some implementations, a clear ring, such as a glass ring, may be inserted into a portion of the exhaust system 190 such that interrogation windows may be omitted. The emitter 122 and detector 124 may be mounted outside of the clear ring on opposing sides.

In other implementations, the absorption spectroscopy measurement system 120 may be a separate component that may be inserted into the exhaust system 190. For instance, the absorption spectroscopy measurement system 120 may include an exhaust tube portion that may be attached upstream of the SCR catalyst 106 and that includes the interrogation windows for the emitter 122 and/or detector 124. In some implementations, the exhaust tube portion may have several interrogation windows that may be used for the emitter 122 and/or detector 124 and that may be selectively sealed when not in use.

Once a sufficient amount of beam attenuation measurements have been taken using the emitter 122 and detector 124, the set of detected beam attenuation data may be used by a controller or data analysis system to generate a sinogram using tomography algorithms. Tomography is the field of repeatedly imaging sections using a penetrating wave and then using various algorithms to reconstruct a cross-sectional view of the subject of the penetrating waves. By combining spectroscopy and tomography using the detected beam attenuation from the emitter 122 and detector 124, a sinogram is created that shows the total attenuation of each measurement in terms of a linear and radial component. Once enough measurements are made in both the linear and radial coordinate systems, the sinogram is fully constructed to reveal the concentration of the species. Using various tomography algorithms, such as Radon transforms, fan-beam projections, etc., the two dimensional cross-sectional view of the species can be re-created and analyzed.

III. Example Absorption Spectroscopy Measurement Systems

Figure 2:
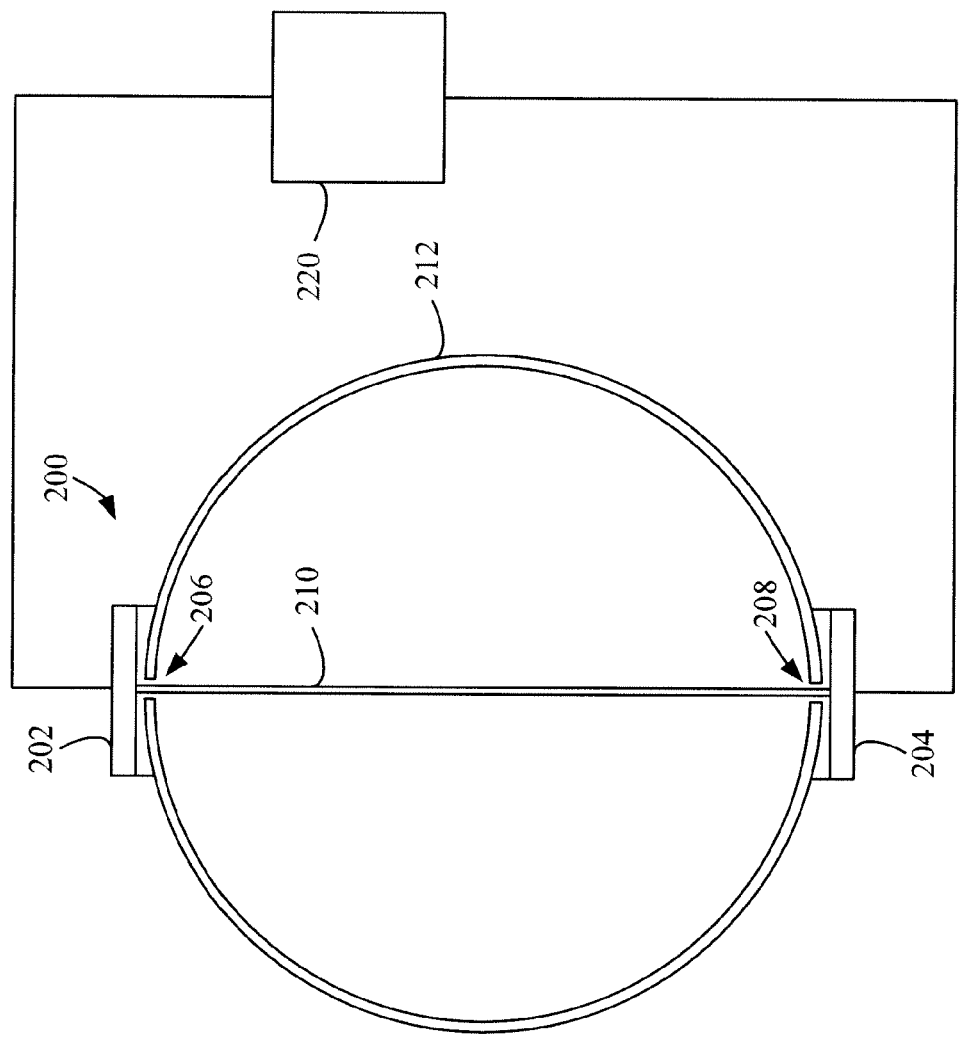
FIG. 2 is a schematic diagram of an example configuration for an absorption spectroscopy measurement system for an exhaust system.

FIG. 2 depicts an example configuration for an absorption spectroscopy measurement system 200 for the exhaust system 190 of FIG. 1. The absorption spectroscopy measurement system 200 includes an emitter 202 and a detector 204. The emitter 202 and the detector 204 are electrically coupled to a controller 220 or data analysis system that is configured control the emitter 202 and receive the detected beam attenuation from the detector 204. The emitter 202 may include an IR-laser that is configured and tuned to measure $NH_3$, for example, HNCO, or any other species to be detected by the absorption spectroscopy measurement system 200. The emitter 202 creates a beam 210 at the specific wavelength as $NH_3$, HNCO, or any other species to be detected. This beam 210 extends through a fluid, such as the exhaust gas within an exhaust pipe portion 212, and the detector 204 measures the relative strength of the beam 210 from the emitter 202. It should be understood that the absorption spectroscopy measurement system 200 may be used with any other fluids and/or systems and is not limited to exhaust gas and/or an exhaust system. The intensity of the beam 210 lost from the emitter 202 to the detector 204 can be correlated to the species' concentration within the exhaust gas from the emitter 202 to the detector 204. This beam attenuation can be measured at several different angles and/or linear locations to develop the two dimensional concentration profiles. Interrogation windows 206, 208 are formed in the exhaust pipe portion 212 to permit the beam 210 emitted from the emitter 202 to go through the exhaust gas and be detected by the detector 204. The interrogation windows 206, 208 may be sized large enough to permit the beam 210 to pass through, but small enough to reduce the amount of exhaust gas that may leak out.

In some implementations, the exhaust pipe portion 212 may be clocked (i.e., rotated) a predetermined angle amount, such as 5 degrees, 10 degrees, 15 degrees, 20 degrees, 25 degrees, 30 degrees, 35 degrees, 40 degrees, 45 degrees, etc., relative to the remainder of the exhaust system such that a subsequent sample of the beam attenuation may be measured at a subsequent angle. In some implementations, the emitter 202 and detector 204 may be moved to other linear locations to develop the two-dimensional concentration profiles. Once enough measurements are made in both the radial and linear coordinate systems, a sinogram is constructed that reveals the concentration of the species, e.g., $NH_3$, HNCO, or any other species to be detected. Various tomography algorithms may be applied to the sinogram data by the controller 220, such as Radon transforms, fan-beam projections, etc., to re-create a cross-sectional view of the species based on the measured beam attenuation values and location data.

Figure 3:
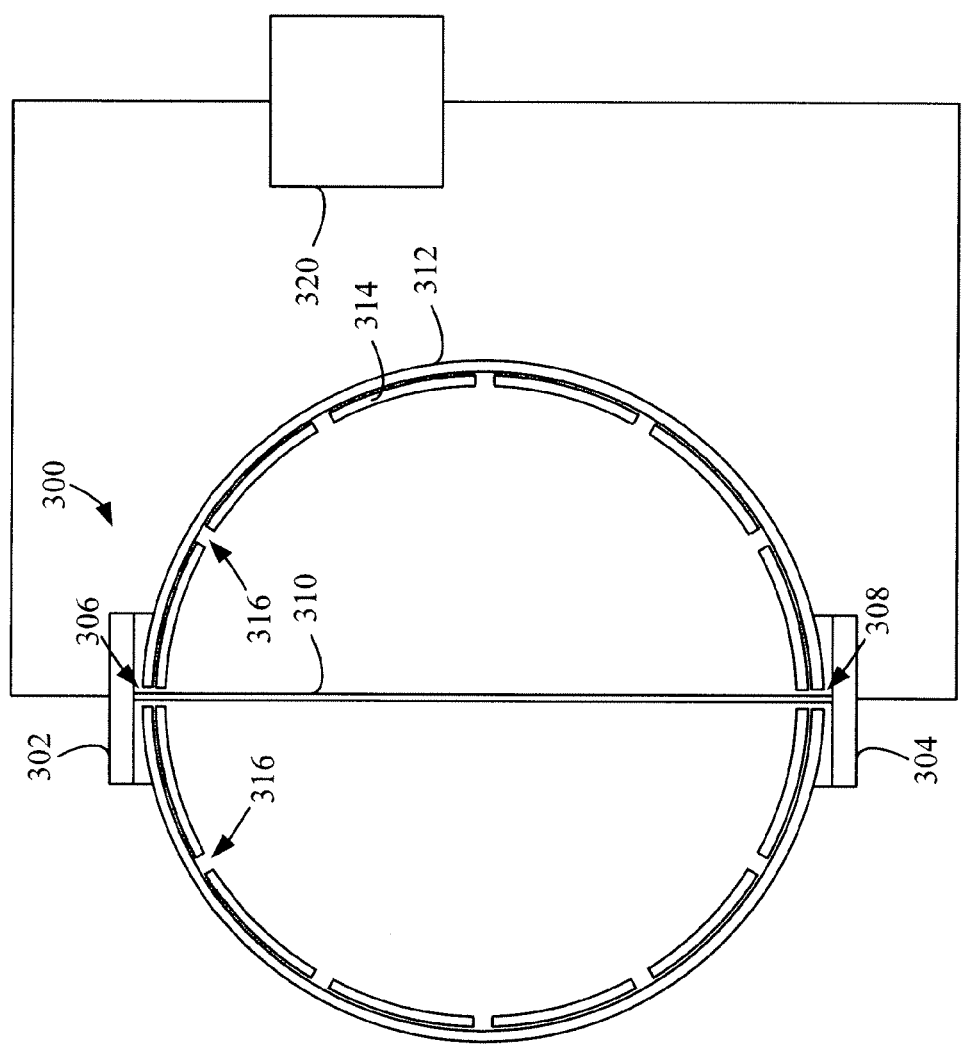
FIG. 3 is a schematic diagram of another example configuration for an absorption spectroscopy measurement system for an exhaust system.

FIG. 3 depicts another absorption spectroscopy measurement system 300 for the exhaust system 190 of FIG. 1. The absorption spectroscopy measurement system 300 includes an emitter 302 and a detector 304. The emitter 302 and detector 304 are electrically coupled to a controller 320 or data analysis system that is configured control the emitter 302 and receive the detected beam attenuation from the detector 304. The emitter 302 may include an IR-laser that is configured and tuned to measure $NH_3$, for example, HNCO, or any other species to be detected by the absorption spectroscopy measurement system 300. The emitter 302 creates a beam 310 at the specific wavelength as $NH_3$, HNCO, or any other species to be detected. This beam 310 extends through the exhaust gas within an inner exhaust pipe portion 314 and the detector 304 measures the relative strength of the beam 310 from the emitter 302. The intensity of the beam 310 lost can then be correlated to the species' concentration within the exhaust gas from the emitter 302 to the detector 304. This beam attenuation can be measured at several different angles and/or linear locations to develop the two dimensional concentration profiles. Main interrogation windows 306, 308 are formed in an outer exhaust pipe portion 312 to permit the beam 310 emitted from the emitter 302 to go through the exhaust gas and be detected by the detector 304. The main interrogation windows 306, 308 may be sized large enough to permit the beam 310 to pass through, but small enough to reduce the amount of exhaust gas that may leak out. In the example shown, an inner exhaust pipe portion 314 may include several inner interrogation windows 316 are predetermined angles, such as 5 degrees, 10 degrees, 15 degrees, 20 degrees, 25 degrees, 30 degrees, 35 degrees, 40 degrees, 45 degrees, etc. Thus, the outer exhaust pipe portion 312 may be rotated relative to the inner exhaust pipe portion to align the main interrogation windows 306, 308 with another set of inner interrogation windows 316. A subsequent sample of the beam attenuation may be measured at the subsequent angle. In some implementations, the emitter 302 and detector 304 may be moved to other linear locations to develop the two-dimensional concentration profiles. Once enough measurements are made in both the radial and linear coordinate systems, a sinogram is constructed that reveals the concentration of the species, e.g., $NH_3$, HNCO, or any other species to be detected. Various tomography algorithms may be applied to the sinogram data by the controller 320, such as Radon transforms, fan-beam projections, etc., to re-create a cross-sectional view of the species based on the measured beam attenuation values and location data.

Figure 4:
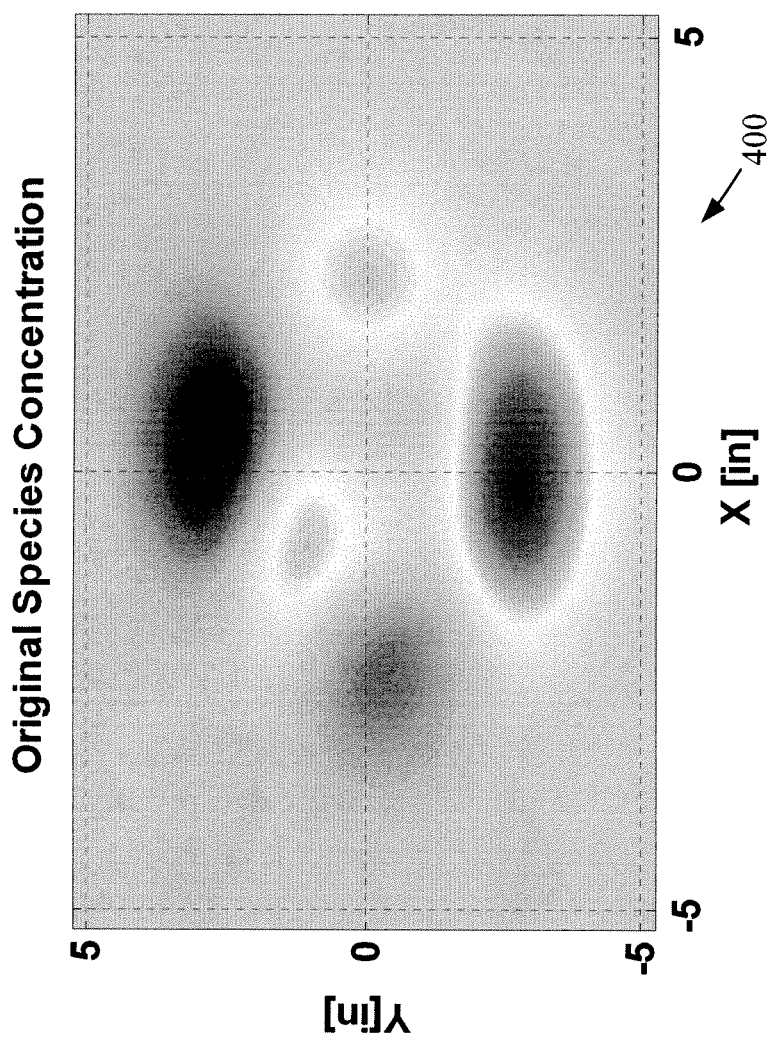
FIG. 4 is a graphical representation of a cross-sectional species concentration of an example sample.

FIG. 4 is a graphical representation 400 of a cross-sectional species concentration, such as $NH_3$ concentration within an exhaust system. The example cross-sectional species concentration depicts regions of high species concentration and low species concentration (e.g., regions within the exhaust where there is a high concentration of ammonia and low concentrations). The graphical representation 400 shows a cross-sectional area spanning from −5 inches in the Y-axis to +5 inches in the Y-axis and −5 inches in the X-axis and +5 inches in the X-axis. The graphical representation 400 may, in some implementations, be for a cylindrical exhaust gas pipe.

Figure 5:
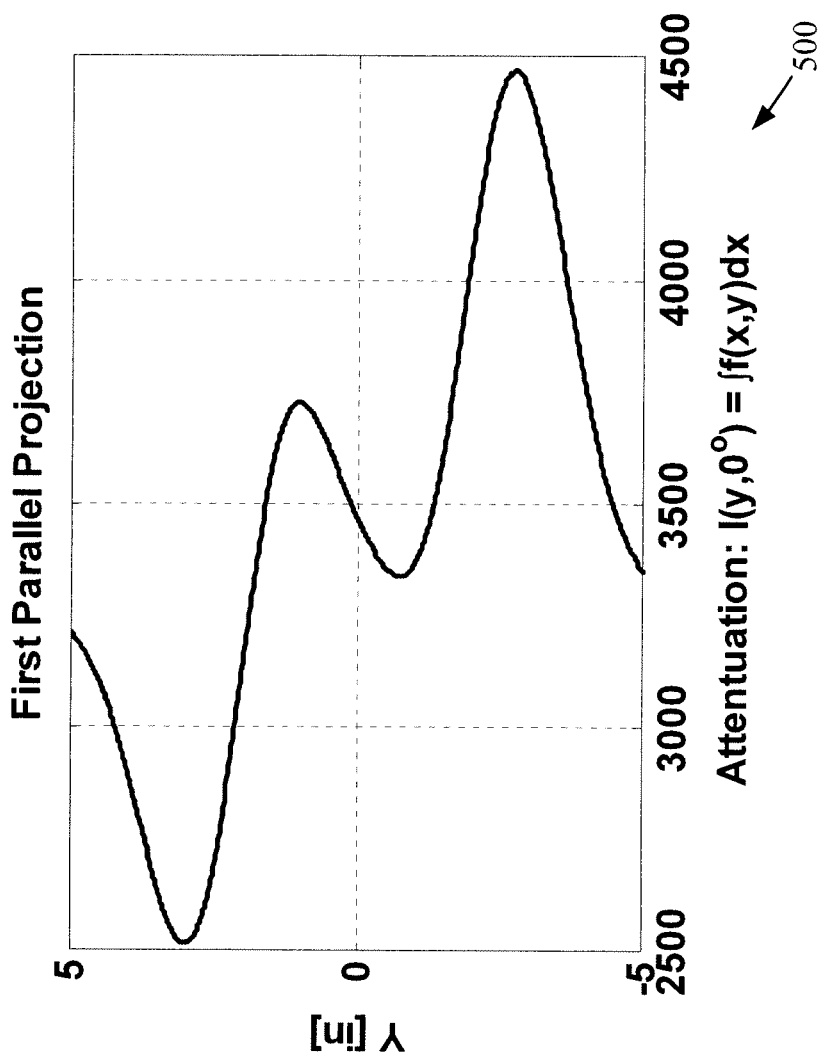
FIG. 5 is a graph of an example parallel projection for the measured attenuation of the example sample.
Figure 6:
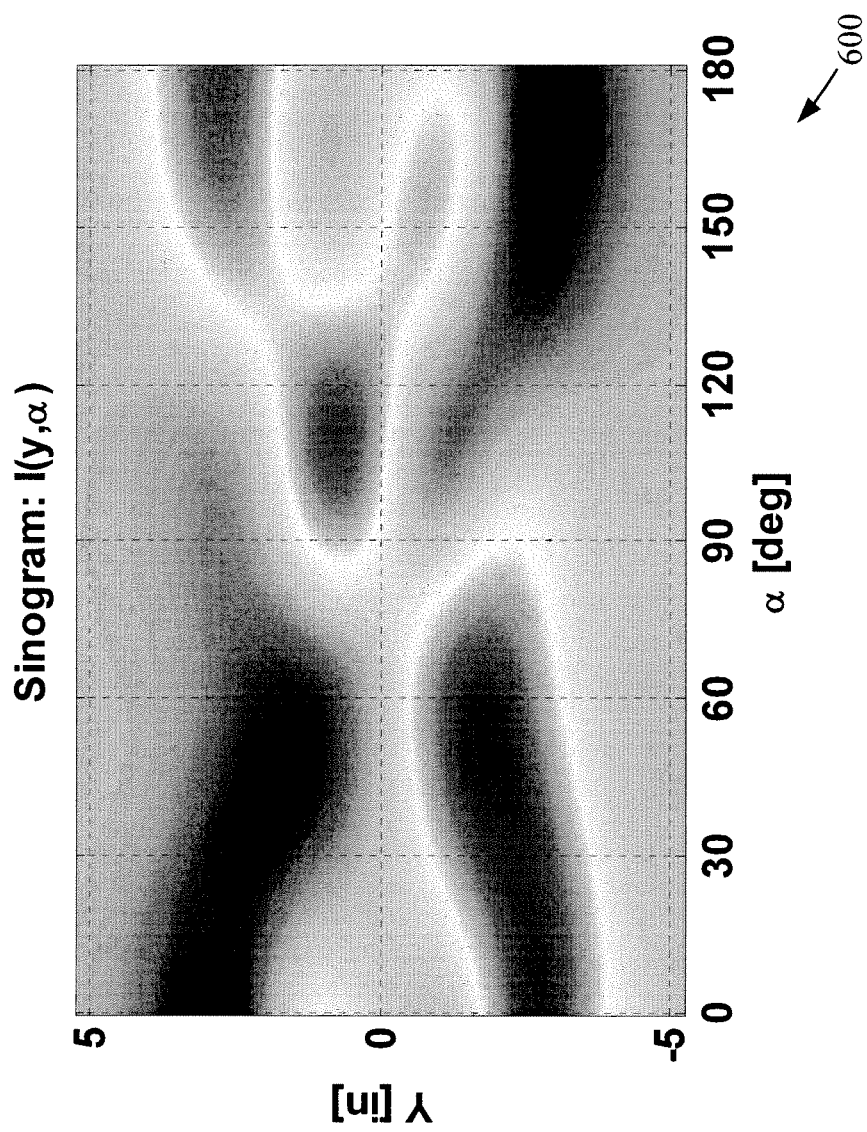
FIG. 6 is a graph of an example sinogram generated for the example sample.
Figure 7:
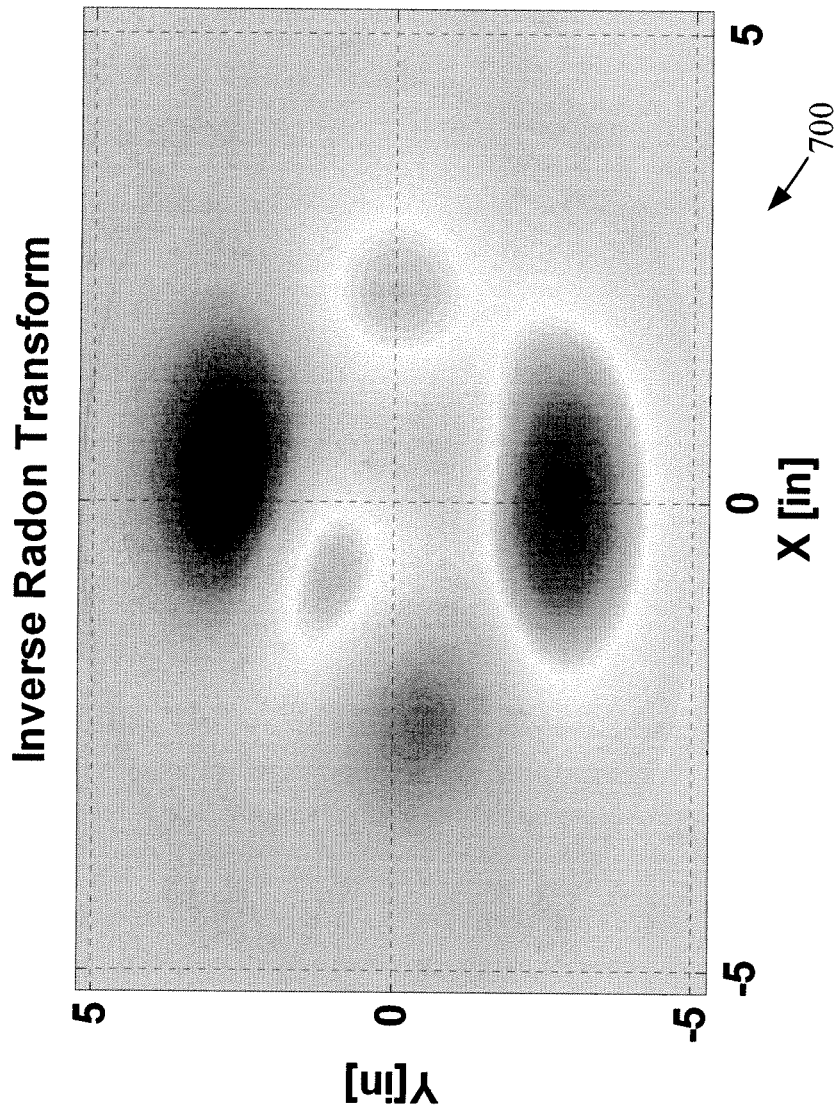
FIG. 7 is a graph of an inverse Radon Transform of the sinogram of FIG. 5.

FIG. 5 is a graph 500 of an example parallel projection for measured attenuation samples of the example sample of FIG. 4 taken at 0 degrees and along the Y-axis from −5 inches to +5 inches. The graph 500 shows the attenuation, I, varying along the Y-axis and corresponding to the high and low concentrations of species from the graphical representation 400 of a cross-sectional species concentration of FIG. 4. A set of attenuation parallel projections can be received by a controller, such as controller 220, 320 of FIGS. 2 and 3, and used to generate a sinogram, such as sinogram 600 of FIG. 6, using tomography. The sinogram 600 includes measurements of attenuation in the Y-axis from −5 inches to +5 inches and from 0 degrees through substantially 180 degrees. In some implementations, the sinogram 600 may be generated with discrete measurements, such as measurements at each Y-axis inch from −5 inches, inclusive, to +5 inches, inclusive and at predetermined angular degrees, such as at 30, 60, 90, 120, 150 and/or 180 degrees. Using the data from the sinogram 600, an inverse Radon Transform may be applied, such as by controller 220, 320, to the sinogram data to generate a depiction 700 of the cross-sectional species concentration measured by the beam attenuation shown in FIG. 7. The depiction 700 of the cross-sectional species concentration is substantially similar to the graphical representation 400 of the cross-sectional species concentration of FIG. 4. The cross-sectional species concentration may be used to evaluate exhaust system and/or component designs, detect obstructions or other problems within existing exhaust systems, indirectly determine the wear on components of existing exhaust system, and/or otherwise assist in improving or diagnosing problems with an exhaust system.

Figure 8:
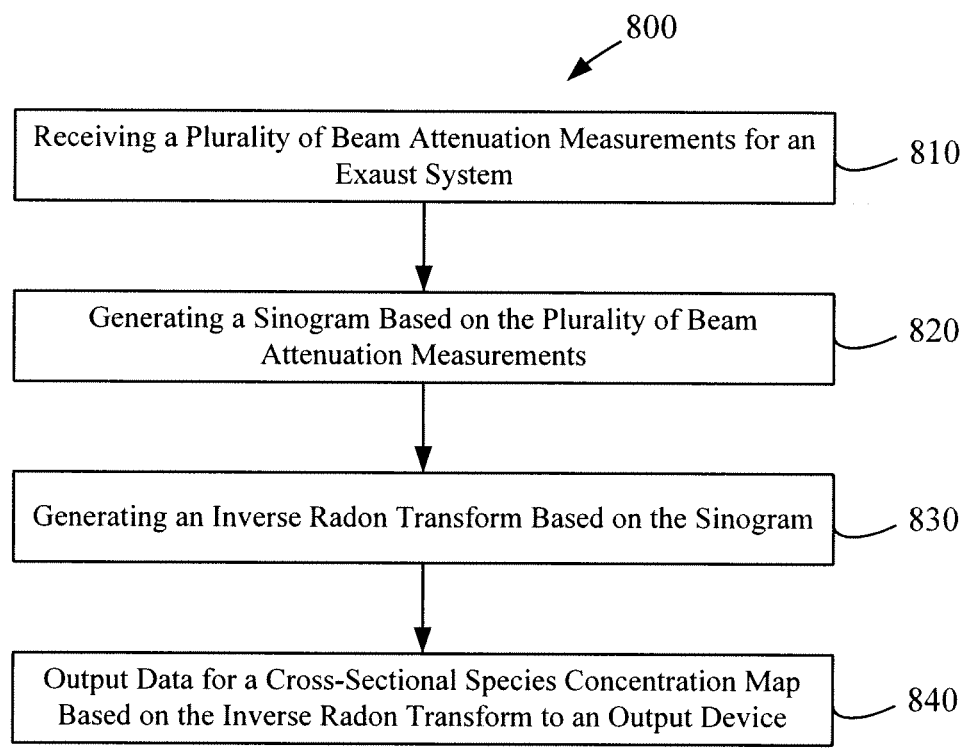
FIG. 8 is a flow diagram of an example method for generating an inverse Radon Transform for an example sample.

FIG. 8 depicts an example method 800 for generating an inverse Radon Transform for a cross-section of an exhaust system. The method includes receiving a plurality of beam attenuation measurements for an exhaust system (block 810). The plurality of beam attenuation measurements may be received by a controller, such as controller 220, 320, from a detector, such as detector 124, 204, 304, detecting the beam attenuation from an emitter 122, 202, 302 tuned to the specific wavelength of a species of interest. For an exhaust system, the emitter 122, 202, 302 may be tuned to the specific wavelength for $NH_3$, HNCO, or any other species to be detected. The plurality of beam attenuation measurements may be at predetermined positions, such as predetermined angular degrees of 30, 60, 90, 120, 150 and/or 180 degrees and predetermined linear positions relative to the exhaust system cross-section.

The method 800 further includes generating a sinogram based on the plurality of beam attenuation measurements (block 820). In some implementations, the controller, such as controller 220, 320, may be configured to receive and store, such as in a tangible and non-transitory computer-readable medium, the plurality of beam attenuation measurements. Once sufficient beam attenuation measurements have been received, the controller may generate a sinogram based on the beam measurements.

The method still further includes generating an inverse Radon Transform based on the sinogram (block 830). The controller, such as controller 220, 320, may apply an inverse Radon Transform algorithm or other tomography algorithm to generate a cross-sectional species concentration map, such as that shown in FIG. 7. In some implementations, the generated cross-sectional species concentration map may be output to a visual display for viewing, stored for later usage, and/or otherwise used. In some implementations, data representative of the cross-sectional species concentration map based on the inverse Radon Transform may be outputted to an output device (block 840). The output device may include a diagnostic system or diagnostic tool. For instance, the diagnostic system may be an on-vehicle diagnostic system, an off-vehicle diagnostic system (e.g., a service diagnostic system), and/or a test diagnostic system (e.g., a testing system for testing various exhaust configurations). In other implementations, the output device may be a monitor, a component associated with an engine in fluid communication with the exhaust system, a component associated with the exhaust system, etc. The outputted data may be used to modify an exhaust system configuration, modify a configuration setting for the exhaust system, modify one or more settings for components affecting the exhaust, modify an injection pressure of a doser, switch a urea doser from an air-assisted mode to an airless mode or vice versa. In some implementations, the absorption spectroscopy measurement system may be utilized with a burner rig, an engine, a fan system, a test apparatus that generates mass flow, etc. Thus, it should be understood that the absorption spectroscopy measurement systems described herein are not limited to engines and/or exhaust systems, but can be utilized with any system to analyze uniformity in a flow.

The term "controller" encompasses all kinds of apparatus, devices, and machines for processing data, including by way of example a programmable processor, a computer, a system on a chip, or multiple ones, a portion of a programmed processor, or combinations of the foregoing. The apparatus can include special purpose logic circuitry, e.g., an FPGA or an ASIC. The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code).

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, the separation of various system components in the implementations described above should not be understood as requiring such separation in all implementations, and it should be understood that the described components and systems can generally be integrated in a single product or packaged into multiple products embodied on tangible media.

As utilized herein, the term "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims. Additionally, it is noted that limitations in the claims should not be interpreted as constituting "means plus function" limitations under the United States patent laws in the event that the term "means" is not used therein.

The terms "coupled," "connected," and the like as used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

The terms "fluidly coupled," "in fluid communication," and the like as used herein mean the two components or objects have a pathway formed between the two components or objects in which a fluid, such as water, air, gaseous reductant, gaseous ammonia, etc., may flow, either with or without intervening components or objects. Examples of fluid couplings or configurations for enabling fluid communication may include piping, channels, or any other suitable components for enabling the flow of a fluid from one component or object to another.

It is important to note that the construction and arrangement of the system shown in the various exemplary implementations is illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A system for species concentration spatial reconstruction for an exhaust system comprising:
   an outer exhaust tube portion and an inner exhaust tube portion, the outer exhaust tube portion rotatable relative to the inner exhaust tube portion, the inner exhaust tube portion comprising a plurality of inner interrogation windows at predetermined angular locations of the inner exhaust tube portion, the outer exhaust tube portion comprising an outer interrogation window selectively aligning with one of the plurality of inner interrogation windows;
   an emitter radially coupled to a first portion of the outer exhaust tube portion, the emitter including a specific wavelength of a species to be measured;
   a detector radially coupled to a second portion of the outer exhaust tube portion, opposite to the first portion, and positioned to detect a beam attenuation of a beam from the emitter; and
   a controller configured to receive a plurality of beam attenuation measurements from the detector and to generate a cross-sectional species concentration map based on the plurality of beam attenuation measurements.

2. The system of claim 1, wherein the emitter is tuned to the specific wavelength of the species to be measured.

3. The system of claim 1, wherein the species is ammonia.

4. The system of claim 1, wherein the controller is further configured to generate a sinogram based on the plurality of beam attenuation measurements, the cross-sectional species concentration map based on the generated sinogram.

5. The system of claim 4, wherein the cross-sectional species concentration map is based on an inverse Radon Transform of the generated sinogram.

6. The system of claim 1, wherein the exhaust system comprises a catalyst.

7. The system of claim 1, wherein the emitter is an IR-laser.

8. An apparatus for NH3 concentration spatial reconstruction for an exhaust system comprising:
    an outer exhaust tube portion and an inner exhaust tube portion, the outer exhaust tube portion rotatable relative to the inner exhaust tube portion, the inner exhaust tube portion comprises a plurality of inner interrogation windows at predetermined angular locations of the inner exhaust tube portion, the outer exhaust tube portion comprising an outer interrogation window selectively aligning with one of the plurality of inner interrogation windows;
    an emitter radially coupled to a first portion of the outer exhaust tube portion, the emitter tuned to a specific wavelength of NH3;
    a detector radially coupled to a second portion of the outer exhaust tube portion, opposite to the first portion, and positioned to detect a beam attenuation of a beam from the emitter; and
    a controller configured to receive a plurality of beam attenuation measurements from the detector and to generate a cross-sectional NH3 concentration map based on the plurality of beam attenuation measurements.

9. The apparatus of claim 8, wherein the first portion and the second portion of the outer exhaust tube portion each comprise an interrogation window.

10. The apparatus of claim 8, wherein the controller is further configured to generate a sinogram based on the plurality of beam attenuation measurements, the cross-sectional NH$_3$ concentration map based on the generated sinogram.

11. The apparatus of claim 10, wherein the cross-sectional species concentration map is based on an inverse Radon Transform of the generated sinogram.

12. The apparatus of claim 8, wherein the exhaust system comprises a catalyst.

13. The apparatus of claim 8, wherein the emitter is an IR-laser.

14. A method for species concentration spatial reconstruction for an exhaust system comprising:
    receiving a first beam attenuation measurement from a detector radially coupled to an outer exhaust tube portion of an exhaust system, the outer exhaust tube portion at a first angular position relative to an inner exhaust tube portion, the inner exhaust tube portion comprising a plurality of inner interrogation windows at predetermined angular locations of the inner exhaust tube portion, the outer exhaust tube portion comprising an outer interrogation window selectively aligned with a first of the plurality of inner interrogation windows, the detector detecting a beam attenuation of an emitter tuned to a specific wavelength of a species to be measured;
    rotating the outer exhaust tube portion relative to the inner exhaust tube portion to a second angular position to selectively align the outer interrogation window with a second of the plurality of inner interrogation windows;
    receiving a second beam attenuation measurement from the detector;
    generating a sinogram based, at least in part, on the first and second beam attenuation measurements; generating a cross-sectional species concentration map based on an inverse Radon Transform of the generated sinogram; and
    outputting data for the generated cross-sectional species concentration map to an output device.

15. The method of claim 14, wherein the species is NH$_3$.

16. The method of claim 15, wherein the emitter is an IR-laser.

17. The method of claim 16, wherein the first and second beam attenuation measurements from the detector are at a position upstream of a catalyst.

18. A tangible computer-readable storage medium having executable instructions stored thereon that, when executed by a processor, cause the processor to:
    process a first received beam attenuation measurement from a detector radially coupled to an outer exhaust tube portion of an exhaust system, the outer exhaust tube portion at a first angular position relative to an inner exhaust tube portion, the inner exhaust tube portion comprising a plurality of inner interrogation windows at predetermined angular locations of the inner exhaust tube portion, the outer exhaust tube portion comprising an outer interrogation window selectively aligned with a first of the plurality of inner interrogation windows, the detector detecting a beam attenuation of an emitter tuned to a specific wavelength of a species to be measured;
    process a second received beam attenuation measurement from the detector when the outer exhaust tube portion is rotated relative to the inner exhaust tube portion to a second angular position, the outer interrogation window selectively aligned with a second of the plurality of inner interrogation windows;
    generate a sinogram based, at least in part, on the first and second beam attenuation measurements; and
    generate a cross-sectional species concentration map based on an inverse Radon Transform of the generated sinogram.

19. The tangible computer-readable storage medium of claim 18, having executable instructions stored thereon that further cause the processor to:
    output data for the generated cross-sectional species concentration map to a diagnostic system.

20. The tangible computer-readable storage medium of claim 19, wherein the species is ammonia or HNCO, the emitter is an IR-laser, and the first and second beam attenuation measurements from the detector are at a position upstream of a catalyst.

* * * * *